(12) United States Patent
Laitala et al.

(10) Patent No.: US 9,736,555 B2
(45) Date of Patent: Aug. 15, 2017

(54) METHOD AND A DEVICE FOR CROSS-TALK CORRECTION OF MEASURED INTENSITIES

(71) Applicant: WALLAC OY, Turku (FI)

(72) Inventors: Ville Petteri Laitala, Turku (FI); Raimo Harju, Turku (FI)

(73) Assignee: WALLAC OY, Turku (FI)

( * ) Notice: Subject to any disclaimer, the term of this patent is extended or adjusted under 35 U.S.C. 154(b) by 5 days.

(21) Appl. No.: 14/784,768

(22) PCT Filed: Apr. 8, 2014

(86) PCT No.: PCT/FI2014/050246
§ 371 (c)(1),
(2) Date: Oct. 15, 2015

(87) PCT Pub. No.: WO2014/170537
PCT Pub. Date: Oct. 23, 2014

(65) Prior Publication Data
US 2016/0066072 A1 Mar. 3, 2016

Related U.S. Application Data

(60) Provisional application No. 61/811,847, filed on Apr. 15, 2013.

(30) Foreign Application Priority Data

Apr. 15, 2013 (FI) ..................................... 20135367

(51) Int. Cl.
*H04Q 11/00* (2006.01)
*C12Q 1/68* (2006.01)
(Continued)

(52) U.S. Cl.
CPC ....... *H04Q 11/0005* (2013.01); *C12Q 1/6818* (2013.01); *G01N 21/274* (2013.01);
(Continued)

(58) Field of Classification Search
USPC .......................................... 398/50
See application file for complete search history.

(56) References Cited

U.S. PATENT DOCUMENTS 7,209,836 B1 4/2007 Schermer et al.
2004/0161165 A1 8/2004 Riley et al.
(Continued)

FOREIGN PATENT DOCUMENTS

WO 98-15830 4/1998

OTHER PUBLICATIONS

Chen et al: "Quantitative FRET data analysis: protein localization in living specimens," Proceedings of SPIE, vol. 6089, Feb. 9, 2006, pp. 60891W-60891W-9.
(Continued)

*Primary Examiner* — David Payne
*Assistant Examiner* — Omar S Ismail
(74) *Attorney, Agent, or Firm* — Young & Thompson (57) ABSTRACT

A method for cross-talk correction of intensities measured on mutually separate detection wavelength bands is presented. Each detection wavelength band relates to one of analyte-specific probe-populations contained by a sample to be analyzed. Each probe-population is capable of emitting a first signal component and a second signal component whose spectra have maxima at different wavelengths and at least the first signal component is dependent on presence of analyte detectable with that probe-population. Cross-talk corrected intensities are computed on the basis of a) the intensities measured on the detection wavelength bands, b) a value indicative of intensity occurring on an auxiliary
(Continued)

wavelength band outside the detection wavelength bands and at least partially caused by the second signal components, and c) pre-determined cross-talk parameters. For example in con-junction with FRET-based assays, the dependency of a background signal on the percentage of hybridized probes can be taken into account in the cross-talk correction.

31 Claims, 4 Drawing Sheets

(51) Int. Cl.
    *G01N 21/27*     (2006.01)
    *G01N 21/64*     (2006.01)

(52) U.S. Cl.
    CPC ..... *G01N 21/6452* (2013.01); *H04Q 11/0003* (2013.01); *C12Q 2537/101* (2013.01); *G01N 2021/6421* (2013.01); *G01N 2021/6441* (2013.01); *H04Q 2011/0049* (2013.01)

(56) References Cited

U.S. PATENT DOCUMENTS

| | | |
|---|---|---|
| 2004/0191794 A1 | 9/2004 | Weindel et al. |
| 2005/0123957 A1 | 6/2005 | Laitala |
| 2006/0147954 A1 | 7/2006 | Laitala et al. |
| 2011/0301062 A1* | 12/2011 | Zhu ................ G01N 21/278 506/12 |
| 2012/0009566 A1* | 1/2012 | Soukka ................ C12Q 1/6818 435/5 |
| 2013/0079236 A1* | 3/2013 | Holmes ................ G01N 33/50 506/9 |

OTHER PUBLICATIONS

Elangovan et al: "Characterization of one- and two-photon excitation fluorescence resonance energy transfer microscopy", Methods, vol. 29, No. 1, 2003, pp. 58-73.

Elder et al: "A quantitative protocol for dynamic measurements of protein interactions by Forster resonance energy transfer-sensitized fluorescence emission," Journal of the Royal Society, vol. 6, No. Suppl. 1, 2009, pp. S59-S81.

Takanishi et al: "GFP-based FRET analysis in live cells," Brain Research, vol. 1091, No. 1, May 26, 2006, pp. 132-139.

* cited by examiner

METHOD AND A DEVICE FOR CROSS-TALK CORRECTION OF MEASURED INTENSITIES

FIELD OF THE DISCLOSURE

The disclosure of this document relates to a method for cross-talk correction of intensities measured on two or more detection wavelength bands from a sample. Furthermore, the disclosure relates to a device and to a computer program for cross-talk correction of intensities measured on two or more detection wavelength bands from a sample. Furthermore, the disclosure relates to a measurement instrument provided with cross-talk correction.

BACKGROUND

A widely used principle in multianalyte assays is to use labeled analyte-specific tracer molecules where concentrations of analytes in a sample can be detected on the basis of changes taking place in fluorescence-based emission signals that may be dependent on one or more excitation wavelengths used. In an ideal case, fluorescence-based emission signals related to different analytes occur on non-overlapping detection wavelength bands and therefore the emission signals can be separated from each other with straightforward optical filtering. However, in many cases, one or more of the spectra of the fluorescence-based emission signals related to different analytes is/are so wide and spectrally overlapping that it is not possible to select such detection wavelength bands that all emission signals measured on these detection wavelength bands would be free from cross-talk.

A simple principle for cross-talk correction is applicable in two-analyte assays where intensity of one of the emission signals can be measured cross-talk free using a suitable temporal detection window and/or a suitable detection wavelength band. The measured intensity of the other emission signal is corrected using the measured intensity of the first emission signal and an empirical cross-talk parameter which indicates the relation between the intensity occurring in the detection wavelength band of the first emission signal and intensity occurring in the detection wavelength band of the other emission signal in a test situation where only the analyte causing the first emission signal is present. When using this method it is worth noticing that the measured intensity of the first emission signal may be at least partially caused by a background signal that is present also when the first emission signal is not generated in detection reactions. Thus, in order to avoid too strong cross-talk correction especially in situations where the first emission signal is not generated, or generated only in a small extent, in detection reactions, the contribution of the background signal should be sufficiently eliminated from the measured intensity of the first emission signal prior to the cross-talk correction. The contribution of the background signal and the cross-talk parameter can be determined on the basis of intensities measured from appropriate test samples.

In many cases the situation is, however, more complicated so that none of the emission signals can be measured cross-talk free, i.e. the emission signals are spectrally and temporally so overlapping that it is not possible to select such temporal detection windows and/or detection wavelength bands so that at least one of the emission signals could be measured cross-talk free. Exemplifying cases where a situation of the kind described above is present are, for example, assays based on time-resolved fluorescence resonance energy transfer "TR-FRET" based multianalyte detection. Details about exemplifying FRET-based detection methods can be found for example from publications US20060147954 and V. Laitala et al., Time-resolved detection probe for homogeneous nucleic acid analyses in one-step format, Analytical Biochemistry 361 (2007) 126-131. In the method described by V. Laitala et al., each FRET-probe comprises a donor, an acceptor, and a reactive region capable of specifically hybridizing with its complementary target sequence, i.e. the target analyte to be detected with the probe under consideration. In the method described by V. Laitala et al., the time-resolved fluorescence emission signal of a population of probes of a given type comprises two signal components: a first signal component belonging to the acceptors excited due to the energy transfer from the excited donors and a second signal component belonging to the excited donors which do not participate to the energy transfer. The acceptor is preferably selected so that its emission spectrum has a maximum at a wavelength where the donor has a local minimum in its emission spectrum. The decay time of the energy transfer induced acceptor emission is dependent on the energy transfer efficiency, which in turn is inversely proportional to distance between the acceptor and the donor. Decay time of energy transfer induced acceptor emission is significantly faster when the probes are unhybridized, i.e. a short donor-acceptor distance, than when the probes are hybridized with the target analyte, i.e. a longer donor-acceptor distance. Thus, acceptor emission signal of hybridized probes can be separated from acceptor emission signal of unhybridized probes using a suitable temporal detection window. Acceptor emission signals of different probes hybridized with different target analytes can be separated from each other by using appropriate detection wavelength bands but, as mentioned above, the cross-talk complicates the situation. The situation is further complicated by the fact that the background emission caused by excited donors that do not participate to the energy transfer is dependent on the percentage of hybridized probes from all probes in a sample under consideration.

SUMMARY

The following presents a simplified summary in order to provide a basic understanding of some aspects of various exemplifying embodiments. The summary is not an extensive overview of the disclosure of this document. It is neither intended to identify key or critical elements of exemplifying embodiments nor to delineate the protection scope. The following summary merely presents some concepts in a simplified form as a prelude to a more detailed description of exemplifying embodiments.

In accordance with the disclosure, there is provided a method for cross-talk correction of intensities measured on two or more detection wavelength bands from a sample to be analyzed. Each detection wavelength band relates to one of analyte-specific probe-populations contained by the sample, and each probe-population is, after excitation, capable of emitting a first signal component and a second signal component whose spectra are mutually different and at least the first signal component is dependent on presence of analyte detectable with that probe-population. In this document, the word "sample" means substance that comprises one or more analytes to be detected and assay reagents needed for the detection, said assay reagents containing the above-mentioned probe-populations.

The method comprises:

computing estimates of cross-talk intensities occurring on the detection wave-length bands and at least partially caused by the second signal components emitted by the probe-populations on the basis of: a) first cross-talk parameters and b) at least one value indicative of at least one intensity occurring on at least one auxiliary wavelength band outside the detection wavelength bands and at least partially caused by the second signal components, and computing cross-talk corrected intensities of the detection wavelength bands on the basis of: a) the intensities measured on the detection wavelength bands, b) the computed estimates of the cross-talk intensities, and c) second cross-talk parameters, wherein:

each of the first cross-talk parameters indicates a relation between a) intensity occurring on one of the detection wavelength bands and at least partially caused by the second signal components, and b) intensity occurring on the auxiliary wavelength band and at least partially caused by the second signal components, and the first cross-talk parameters being obtained on the basis of first test intensities measurable from one or more first model samples each of which contains one or more of the analyte-specific probe-populations and is free from analytes detectable with the probe-populations, and each of the second cross-talk parameters indicates a relation between a) intensity occurring on the detection wavelength band related to one of the probe-populations and at least partially caused by the first signal component emitted by another of the probe-populations, and b) intensity occurring on the detection wavelength band related to the other of the probe-populations and at least partially caused by the first signal component emitted by the other of the probe-populations.

The probe-populations can be, for example but not necessarily, populations of probes based on the fluorescence resonance energy transfer "FRET". The method for cross-talk correction can be used, for example, in conjunction with time-resolved fluorescence resonance energy transfer "TR-FRET" based multianalyte detections that are suitable for e.g. Severe Combined Immunodeficiency "SCID" assays.

In a method according to an advantageous but non-limiting embodiment, the value indicative of the intensity occurring on the auxiliary wavelength band and at least partially caused by the second signal components has a value measured from the sample on the auxiliary wavelength band. Therefore, for example in conjunction with FRET-based assays, the dependency of the background emission on the percentage of hybridized probes from all probes can be taken into account in the cross-talk correction. In a case, where assay is carried out in mictotiter wells containing samples, the intensity occurring on the auxiliary wavelength band and at least partially caused by the second signal components is preferably measured from each sample well separately.

In accordance with the disclosure, there is provided also a device for cross-talk correction of intensities measured on two or more detection wavelength bands from a sample to be analyzed. Each detection wavelength band relates to one of analyte-specific probe-populations contained by the sample, and each probe-population is, after excitation, capable of emitting a first signal component and a second signal component whose spectra are mutually different and at least the first signal component is dependent on presence of analyte detectable with that probe-population. The device comprises a computing system configured to:

compute estimates of cross-talk intensities occurring on the detection wave-length bands and at least partially caused by the second signal components emitted by the probe-populations on the basis of: a) first cross-talk parameters and b) at least one value indicative of at least one intensity occurring on at least one auxiliary wavelength band outside the detection wavelength bands and at least partially caused by the second signal components, and compute cross-talk corrected intensities of the detection wavelength bands on the basis of: a) the intensities measured on the detection wavelength bands, b) the computed estimates of the cross-talk intensities, and c) second cross-talk parameters, wherein:

each of the first cross-talk parameters indicates a relation between a) intensity occurring on one of the detection wavelength bands and at least partially caused by the second signal components, and b) intensity occurring on the auxiliary wavelength band and at least partially caused by the second signal components, and the first cross-talk parameters being obtained on the basis of first test intensities measurable from one or more first model samples each of which contains one or more of the analyte-specific probe-populations and is free from analytes detectable with the probe-populations, and each of the second cross-talk parameters indicates a relation between a) intensity occurring on the detection wavelength band related to one of the probe-populations and at least partially caused by the first signal component emitted by another of the probe-populations, and b) intensity occurring on the detection wavelength band related to the other of the probe-populations and at least partially caused by the first signal component emitted by the other of the probe-populations.

In accordance with the disclosure, there is provided also an instrument comprising:

measurement equipment for measuring intensities on two or more detection wavelength bands from a sample to be analyzed, and a device according to the disclosure for cross-talk correction of the intensities measured on the two or more detection wavelength bands from the sample.

In accordance with the disclosure, there is provided also a computer program for cross-talk correction of intensities measured on two or more detection wave-length bands from a sample to be analyzed. The computer program comprises computer executable instructions for controlling a programmable processor to:

compute estimates of cross-talk intensities occurring on the detection wave-length bands and at least partially caused by the second signal components emitted by the probe-populations on the basis of: a) first cross-talk parameters and b) at least one value indicative of at least one intensity occurring on at least one auxiliary wavelength band outside the detection wavelength bands and at least partially caused by the second signal components, and compute cross-talk corrected intensities of the detection wavelength bands on the basis of: a) the intensities measured on the detection wavelength bands, b) the computed estimates of the cross-talk intensities, and c) second cross-talk parameters, wherein:
each of the first cross-talk parameters indicates a relation between a) intensity occurring on one of the detection wavelength bands and at least partially caused by the second signal components, and b) intensity occurring on the auxiliary wavelength band and at least partially caused by the second signal components, and the first cross-talk parameters being obtained on the basis of first test intensities measurable from one or more first model samples each of which contains one or more of the analyte-specific probe-populations and is free from analytes detectable with the probe-populations, and each of the second cross-talk parameters indicates a relation between a) intensity occurring on the detection wavelength band related to one of the probe-populations and at least partially caused by the first signal component emitted by another of the probe-populations, and b) intensity occurring on the detection wavelength band related to the other of the probe-populations and at least partially caused by the first signal component emitted by the other of the probe-populations.

A computer program product according to the disclosure comprises a non-volatile computer readable medium, e.g. a compact disc ("CD"), encoded with a computer program according to the disclosure.

A number of exemplifying embodiments are described in accompanied dependent claims.

Various exemplifying embodiments both as to constructions and to methods of operation, together with additional objects and advantages thereof, will be best understood from the following description of specific exemplifying embodiments when read in connection with the accompanying drawings.

The verbs "to comprise" and "to include" are used in this document as open limitations that neither exclude nor require the existence of unrecited features. The features recited in depending claims are mutually freely combinable unless otherwise explicitly stated.

BRIEF DESCRIPTION OF THE FIGURES

The exemplifying embodiments and their advantages are explained in greater detail below in the sense of examples and with reference to the accompanying drawings, in which:

FIG. 3b shows schematic illustration of a view seen downwards from the line A-A of FIG. 3a.

DESCRIPTION OF EXEMPLIFYING EMBODIMENTS

Figure 1:
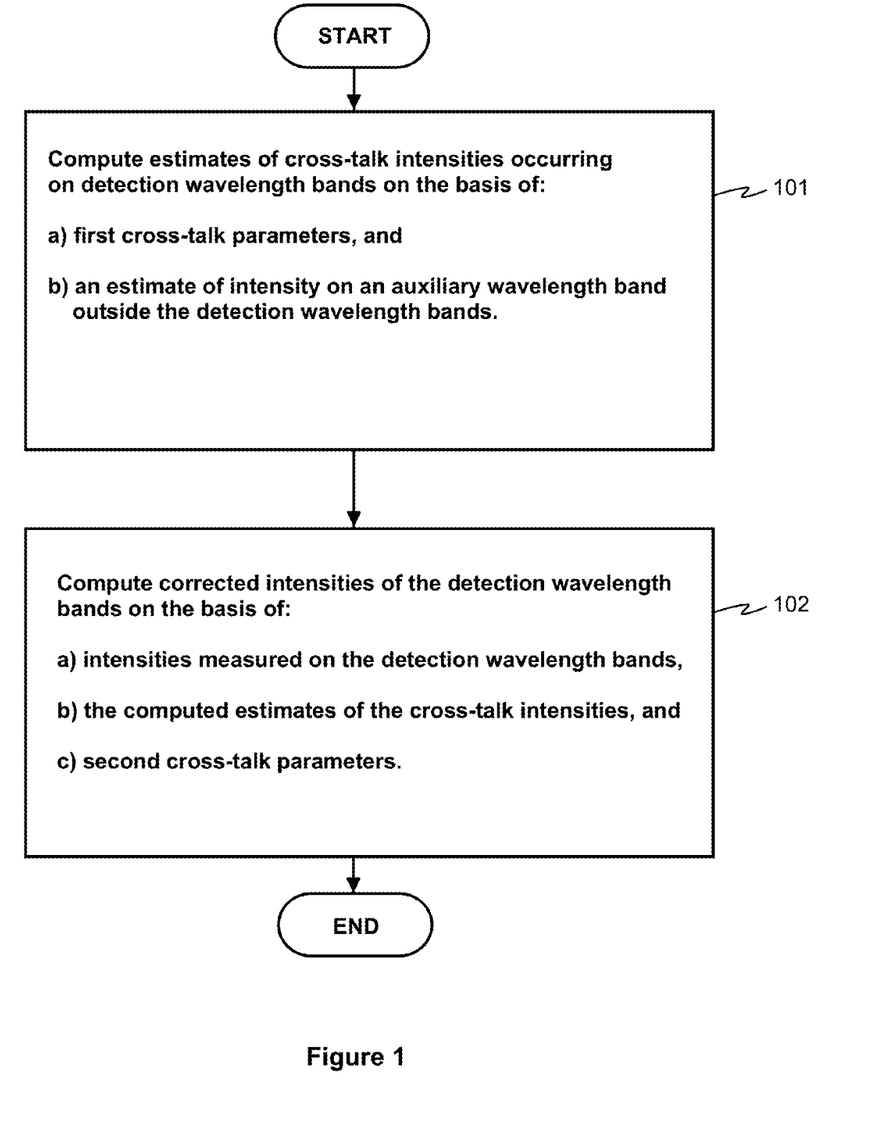
FIG. 1 shows a flow chart of a method according to an exemplifying embodiment for cross-talk correction of intensities measured on two or more detection wavelength bands from a sample to be analyzed.
Figure 2:
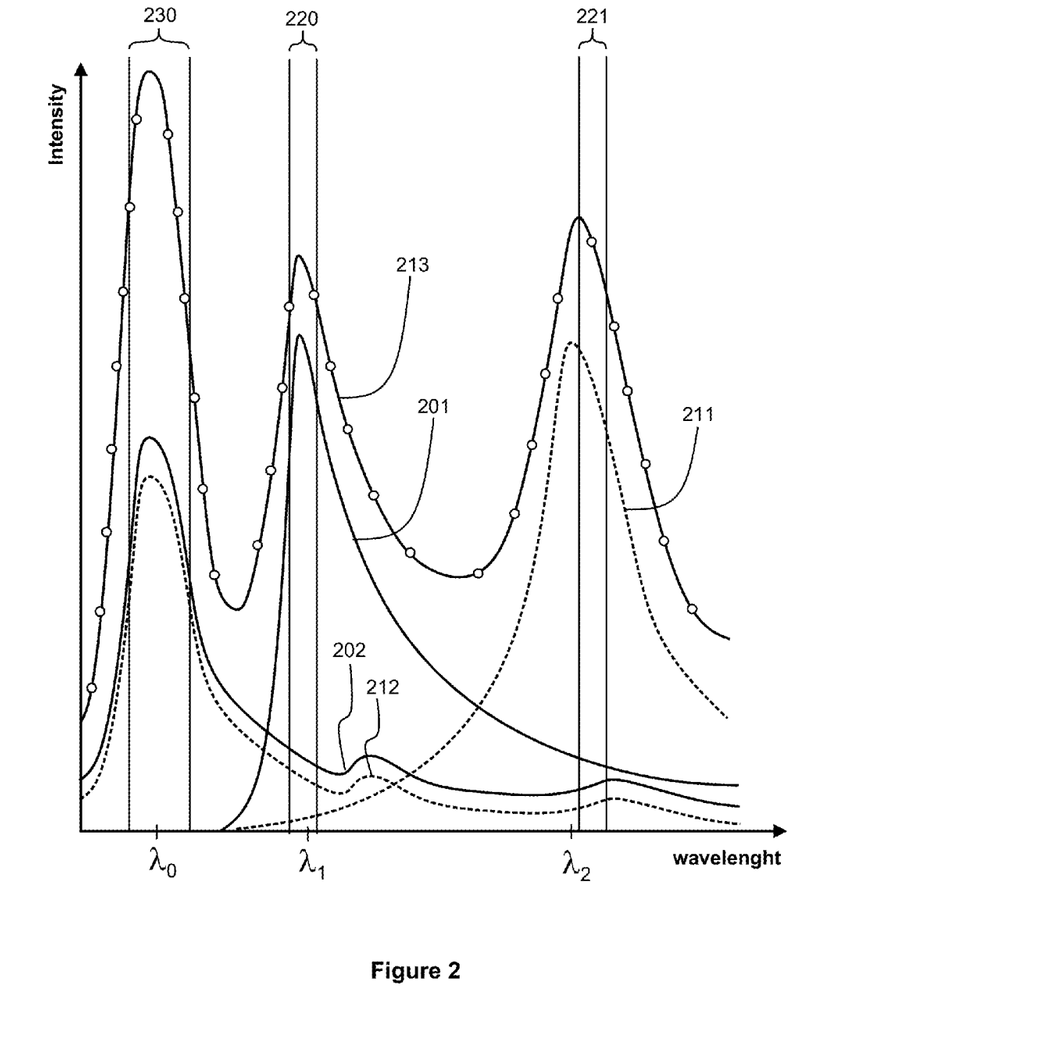
FIG. 2 illustrates emission spectra of two probe-populations in an exemplifying case where a method according to an exemplifying embodiment for cross-talk correction is applicable.

FIG. 1 shows a flow chart of a method according to an exemplifying embodiment for cross-talk correction of intensities measured, from a sample to be analyzed, on mutually non-overlapping detection wavelength bands. Each of the detection wavelength bands relates to one of analyte-specific probe-populations contained by the sample. An emission signal of each probe-population contains a first signal component whose spectrum has a maximum at a wavelength specific to that probe-population and which is dependent on concentration of analyte detectable with that probe-population and a second signal component whose spectrum is different from the spectrum of the above-mentioned first signal component. FIG. 2 illustrates emission spectra in an exemplifying case where there are probe-populations $P_1$ and $P_2$. A solid line 213 provided with circles represents the aggregate, i.e. the sum, of the emission spectra of the probe-populations $P_1$ and $P_2$. The aggregate of the emission spectra represents the spectrum of the signal that can be measured from the sample when using a certain excitation wavelength. A solid line 201 represents the spectrum of the first signal component emitted by the probe-population $P_1$, and a solid line 202 represents the spectrum of the second signal component emitted by the probe-population $P_1$. A dashed line 211 represents the spectrum of the first signal component emitted by the probe-population $P_2$ and a dashed line 212 represents the spectrum of the second signal component emitted by the probe-population $P_2$. A wavelength band 220 shown in FIG. 2 represents the detection wavelength band related to the probe-population $P_1$, and a wavelength band 221 represents the detection wavelength band related to the probe-population $P_2$.

The probe-populations $P_1$ and $P_2$ can be, for example but not necessarily, populations, i.e. groups, of probes based on fluorescence resonance energy transfer "FRET" where each probe may comprise at least one donor, at least one acceptor, and at least one reactive region capable of interacting with the analyte to be detected with that probe. The donor and the acceptor of a probe can be attached to a same molecule but it is also possible that a probe comprises a donor attached to a first molecule and an acceptor attached to a second, separate, molecule. In this case, the mutually separate donor and acceptor can interact with the analyte to be detected and thereby form a donor-acceptor pair suitable for e.g. the fluorescence resonance energy transfer "FRET". The donor can be a luminescent label having luminescent lifetime longer than e.g. 1 μs. Each of the probes may comprise, for example, a lanthanide chelate donor and an organic fluorophore acceptor. The lanthanide can be, for example, europium "Eu", terbium "Tb", dysprosium "Dy", or samarium "Sm". The acceptor of the probe-population $P_1$ can be, for example, Alexa Fluor® 647 dye and the acceptor of the probe-population $P_2$ can be, for example, Alexa Fluor® 750 dye. In this case, the values of $\lambda_0$, $\lambda_1$, and $\lambda_2$ shown in FIG. 2 would be $\lambda_0 \approx 615$ nm, $\lambda_1 \approx 665$ nm, and $\lambda_2 \approx 780$ nm, where $\lambda_0$ is the center point of a 610-620 nm auxiliary wavelength band 230 shown in FIG. 2, $\lambda_1$ is the center point of the 660-670 nm detection wavelength band 220, and $\lambda_2$ is the center point of the 775-785 nm detection wavelength band 221. The spectrum depicted with the solid line 201 is caused by the Alexa Fluor® 647 acceptors of the probes of the probe-population $P_1$ excited due to the energy transfer from the excited Eu donors of these probes, and the spectrum depicted with the solid line 202 is caused by the excited Eu donors of the probes of the probe-population $P_1$ not participating to the energy transfer. Correspondingly, the spectrum depicted with the dashed line 211 is caused by the Alexa Fluor® 750 acceptors of the probes of the probe-population $P_2$ excited due to the energy transfer from the excited Eu donors of the probes of the probe-population $P_2$, and the spectrum depicted with the dashed line 212 is caused by the excited Eu donors of the probes of the probe-population $P_2$ not participating to the energy transfer. FIG. 2 can be deemed to represent a time instant after donor excitation when signals emitted by acceptors of unhybridized, i.e. free, probes have already been decayed off sufficiently from the viewpoint of detection.

A method according to an exemplifying embodiment for cross-talk correction of intensities $I_{M1}$ and $I_{M2}$ measured on the detection wavelength bands 220 and 221, respectively, comprises the following actions:

action 101, FIG. 1: computing estimates of cross-talk intensities $C_{B1}$ and $C_{B2}$ occurring on the detection wavelength bands 220 and 221 and at least partially caused by the second signal components emitted by the probe-populations $P_1$ and $P_2$ on the basis of: a) first cross-talk parameters $R_{B1}$ and $R_{B2}$ and b) a value $I_{BM}$ indicative of intensity at least partially caused by the second signal components and occurring on the auxiliary wavelength band 230, FIG. 2, outside the detection wavelength bands 220 and 221, and action 102, FIG. 1: computing cross-talk corrected intensities $I_{C1}$ and $I_{C2}$ of the detection wavelength bands 220 and 221 on the basis of: a) the intensities $I_{M1}$ and $I_{M2}$ measured on the detection wavelength bands 220 and 221, b) the computed estimates of the cross-talk intensities $C_{B1}$ and $C_{B2}$, and c) second cross-talk parameters $R_{12}$ and $R_{21}$.

In conjunction with the time-resolved fluorescence resonance energy transfer "TR-FRET" based multianalyte detection, the above-mentioned cross-talk intensities $C_{B1}$ and $C_{B2}$ can be called "background" intensities so as to be coherent with phraseology related to TR-FRET.

The cross-talk parameter $R_{B1}$ indicates a relation between a) intensity occurring on the detection wavelength band 220 and at least partially caused by the second signal components emitted by the probe-populations $P_1$ and $P_2$, and b) intensity occurring on the auxiliary wavelength band 230 and at least partially caused by the second signal components. Correspondingly, the cross-talk parameter $R_{B2}$ indicates a relation between a) intensity occurring on the detection wavelength band 221 and at least partially caused by the second signal components, and b) intensity occurring on the auxiliary wavelength band 230 and at least partially caused by the second signal components. In a more general case, it is possible that the spectra of the second signal components emitted by different probe-populations are different from each other, e.g. the spectrum of the second signal component of the probe-population $P_1$ can be different from that of the second signal component of the probe-population $P_2$. In this case, better cross-talk correction accuracy can be achieved if it is possible to find such auxiliary wavelength bands so that the intensities occurring on the auxiliary wavelength band and caused by the second signal components are sufficiently free from mutual cross-talk and from cross-talk from the first signal components. The above-presented principle for defining the first cross-talk parameters can be used also in this case but, naturally, when there is more than one the auxiliary wavelength band, the number of the first cross-talk parameters is higher.

The cross-talk parameter $R_{12}$ indicates a relation between a) intensity occurring on the detection wavelength band 220 and at least partially caused by the first signal component emitted by the probe-population $P_2$, and b) intensity occurring on the detection wavelength band 221 and at least partially caused by the first signal component emitted by the probe-population $P_2$. Correspondingly, the cross-talk parameter $R_{21}$ indicates a relation between a) intensity occurring on the detection wavelength band 221 and at least partially caused by the first signal component emitted by the probe-population $P_1$, and b) intensity occurring on the detection wavelength band 220 and at least partially caused by the first signal component emitted by the probe-population $P_1$.

In a method according to an exemplifying embodiment, the value $I_{BM}$ indicative of the intensity occurring on the auxiliary wavelength band 230 and at least partially caused by the second signal components of the probe-populations $P_1$ and $P_2$ is a value measured on the auxiliary wavelength band from the sample to be analyzed. Therefore, for example in conjunction with FRET-based assays where the intensity of signal caused by the second signal components is at least partially dependent on the concentrations of the analytes present in the sample, the $I_{BM}$ can be measured and taken into account in the cross-talk correction from each sample well separately. In a method according to another exemplifying embodiment, the value $I_{BM}$ indicative of the intensity occurring on the auxiliary wavelength band 230 and at least partially caused by the second signal components is a same pre-determined value in conjunction with several samples, e.g. a same value $I_{BM}$ can be used for many sample wells.

In a method according to an exemplifying embodiment, the estimates of the cross-talk intensities $C_{B1}$ and $C_{B2}$ are computed according to the following equation:

$$C_{B1}=R_{B1} \times I_{BM} \text{ and } C_{B2}=R_{B2} \times I_{BM}. \tag{1}$$

In a general case, where there can be two or more analyte-specific probe-populations, the estimate of the cross-talk intensity occurring on the $i^{th}$ one of the detection wavelength bands and at least partially caused by the second signal components of the two or more probe-populations can be computed according to the following equation:

$$C_{Bi}=R_{Bi} \times I_{BM}, \tag{2}$$

where i=1, 2, . . . , the number of the analyte-specific probe-populations, $C_{Bi}$ is the estimate of the cross-talk intensity occurring on the $i^{th}$ one of the detection wavelength bands and at least partially caused by the second signal components, and $R_{Bi}$ is the first cross-talk parameter indicating a relation between a) intensity occurring on the $i^{th}$ one of the detection wavelength bands and at least partially caused by the second signal components, and b) intensity occurring on the auxiliary wavelength band 230 and at least partially caused by the second signal components.

In a method according to an exemplifying embodiment, the cross-talk corrected intensities $I_{C1}$ and $I_{C2}$ of the detection wavelength bands 220 and 221 are solved from the following pair of equations:

$$\begin{cases} I_{C1} = I_{M1} - R_{12}(I_{C2} - C_{B2}) \\ I_{C2} = I_{M2} - R_{21}(I_{C1} - C_{B1}) \end{cases}. \tag{3}$$

In a general case, where there can be three or more analyte-specific probe-populations, the cross-talk corrected intensities of the detection wavelength bands can be solved from the following set of equations:

$$\begin{cases} I_{C1} = I_{M1} - \sum_{j=2}^{n} R_{1j}(I_{Cj} - C_{Bj}) \\ \quad \ldots \\ I_{Ci} = I_{Mi} - \sum_{j=1, j \neq i}^{n} R_{ij}(I_{Cj} - C_{Bj}) \\ \quad \ldots \\ I_{Cn} = I_{Mn} - \sum_{j=1}^{n-1} R_{nj}(I_{Cj} - C_{Bj}) \end{cases} \quad (4)$$

where:

n is the number of the analyte-specific probe-populations, $I_{Ci}$ and $I_{Cj}$ are the cross-talk corrected intensities of the $i^{th}$ and $j^{th}$ ones of the detection wavelength bands, respectively, $I_{Mi}$ is the intensity measured on the $i^{th}$ one of the detection wavelength bands, $C_{Bj}$ is the estimate of the cross-talk intensity occurring on the $j^{th}$ one of the detection wavelength bands and at least partially caused by the second signal components, and $R_{ij}$ is the second cross-talk parameter that indicates a ratio between a) intensity occurring on the $i^{th}$ one of the detection wavelength bands and at least partially caused by the first signal component emitted by the probe-population related to the $j^{th}$ one of the detection wavelength bands and b) intensity occurring on the $j^{th}$ one of the detection wavelength bands and at least partially caused by the first signal component emitted by the probe-population related to the $j^{th}$ one of the detection wavelength bands.

A method according to an exemplifying embodiment comprises determining the first cross-talk parameters on the basis of first test intensities measured from one or more first model samples each of which contains one or more of the probe-populations and is free from analytes detectable with the probe-populations. The first cross-talk parameters can be computed, for example, according to the equation:

$$R_{Bi} = \frac{I_{Model0,i}}{I_{Model0,B}} \quad (5)$$

where:

i=1, 2, . . . , the number of the analyte-specific probe-populations, $R_{Bi}$ is the first cross-talk parameter related to the $i^{th}$ one of the detection wavelength bands, e.g. one of the wavelength bands 220 and 221 shown in FIG. 2, $I_{Model0,i}$ is the first test intensity occurring on $i^{th}$ one of the detection wavelength bands and at least partially caused by the second signal components and measured from such a first model sample that contains the probe-populations, and $I_{model0,B}$ is the first test intensity occurring on the auxiliary wavelength band, e.g. the wavelength band 230 shown in FIG. 2, and at least partially caused by the second signal components and measured from the first model sample.

A method according to an exemplifying embodiment comprises determining the second cross-talk parameters on the basis of second test intensities measured from second model samples, where each of the second model samples contains one or more of the probe-populations and analyte detectable with one of the probe-populations and is free from analytes detectable with the other probe-populations. The second cross-talk parameters can be computed, for example, according to the equation:

$$R_{ij} = \frac{I_{Model,i,j} - C_i}{I_{Model,j,j} - C_j} \quad (6)$$

where:

i=1, 2, . . . , the number of the analyte-specific probe-populations, j=1, 2, . . . , the number of the analyte-specific probe-populations, and i≠j, $R_{ij}$ is the second cross-talk parameter related to the $i^{th}$ and $j^{th}$ ones of the detection wavelength bands, e.g. the wavelength bands 220 and 221 shown in FIG. 2, $I_{Model, i,j}$ is the second test intensity occurring on the $i^{th}$ one of the detection wavelength bands and at least partially caused by the first signal component emitted by the probe-population related to the $j^{th}$ one of the detection wavelength bands and measured from a such second model sample that contains analyte detectable with the probe-population related to the $j^{th}$ one of the detection wavelength bands and is free from analytes detectable with the other probe-populations, $I_{Model, j,j}$ is the second test intensity occurring on the $j^{th}$ one of the detection wavelength bands and at least partially caused by the first signal component emitted by the probe-population related to the $j^{th}$ one of the detection wavelength bands and measured from the above-mentioned second model sample, and $C_i$ and $C_j$ are real valued adjustment terms.

In a method according to an exemplifying embodiment, the above-mentioned $C_i = R_{Bi} \times$ test intensity $I_{Model, B,j}$ at least partially caused by the second signal components and measured on the auxiliary wavelength band from the above-mentioned second model sample, and the above-mentioned $C_j = R_{Bj} \times$ the test intensity $I_{Model B,j}$, where $R_{Bi}$ and $R_{Bj}$ are the first cross-talk parameters related to the $i^{th}$ and $j^{th}$ ones of the detection wavelength bands, respectively.

In a method according to an exemplifying embodiment, $C_i$ is test intensity $I_{Model0,i}$ occurring on $i^{th}$ one of the detection wavelength bands and at least partially caused by the second signal components, and $C_j$ is test intensity $I_{Model0,j}$ occurring on $j^{th}$ one of the detection wavelength bands and at least partially caused by the second signal components, where the test intensities $C_i$ and $C_j$ are measured from a model sample that contains the probe-populations and is free from analytes detectable with the probe-populations.

In a method according to an exemplifying embodiment, the real valued adjustment terms $C_i$ and $C_j$=0.

In a method according to an exemplifying embodiment, the first and second cross-talk parameters are selected from among pre-determined values on the basis of at least one of the following: ways of conduct of intensity measurements, information identifying a measurement instrument used for the intensity measurements. A way of conduct of intensity measurement can be characterized by, for example but not necessarily, the number of successive excitation-counting cycles used in detection of intensity on a certain measurement wavelength band, where each excitation-counting cycle contains an excitation phase and a subsequent counting phase. The information identifying a measurement instrument can be, for example, a serial number of the measurement instrument used for the intensity measurements.

A computer program according to an exemplifying embodiment comprises computer executable instructions for controlling a programmable processor to carry out a method according to any of the above-described exemplifying embodiments. The computer executable instructions can be generated with a suitable programming language.

A computer program product according to an exemplifying embodiment comprises a non-volatile computer readable medium, e.g. a compact disc ("CD"), encoded with a computer program according to an embodiment.

A signal according to an exemplifying embodiment is encoded to carry information defining a computer program according to an embodiment.

Figure 3A:
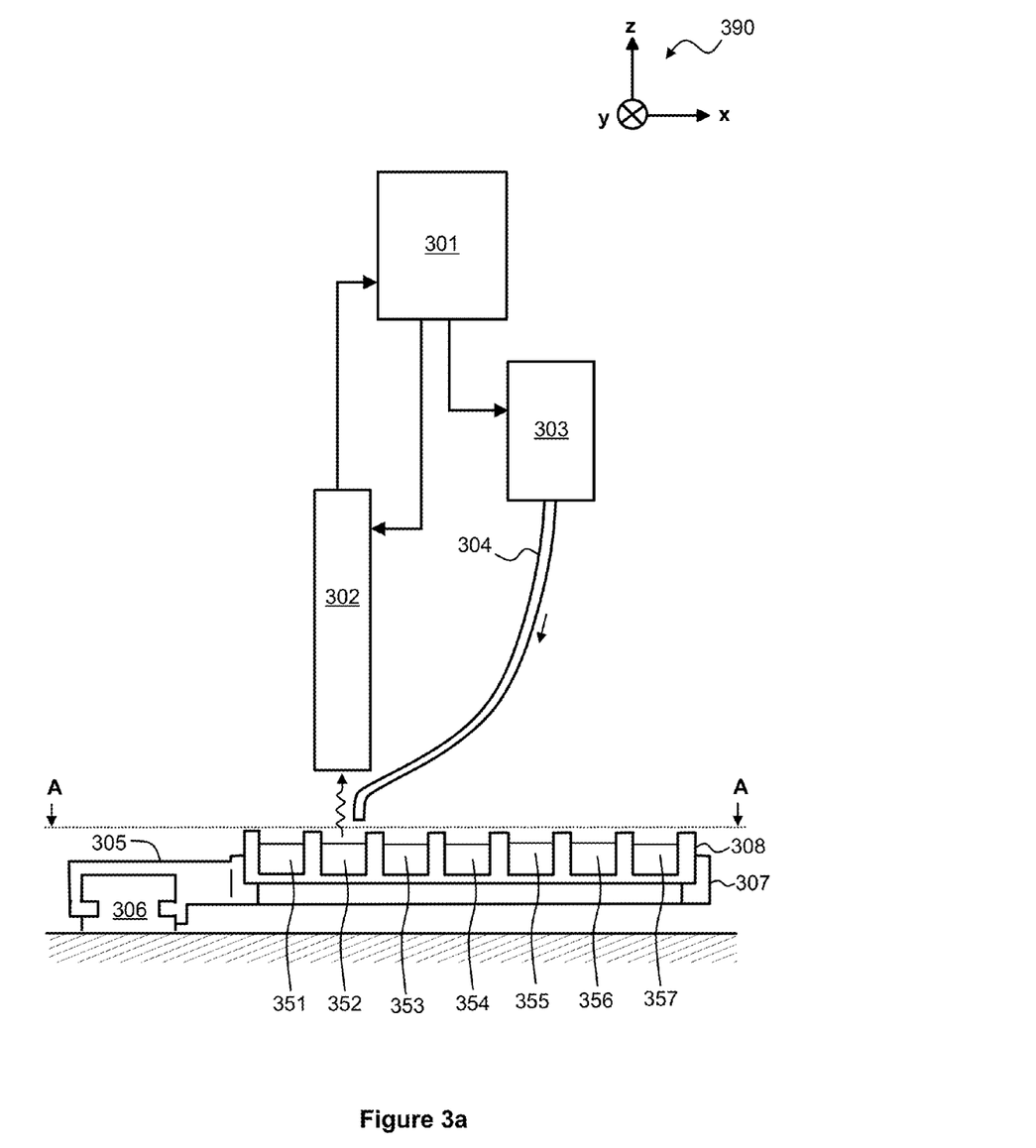
FIG. 3a shows a schematic illustration of an optical measurement instrument comprising a device according to an exemplifying embodiment for cross-talk correction of intensities measured on two or more detection wavelength bands from a sample to be analyzed.
Figure 3B:
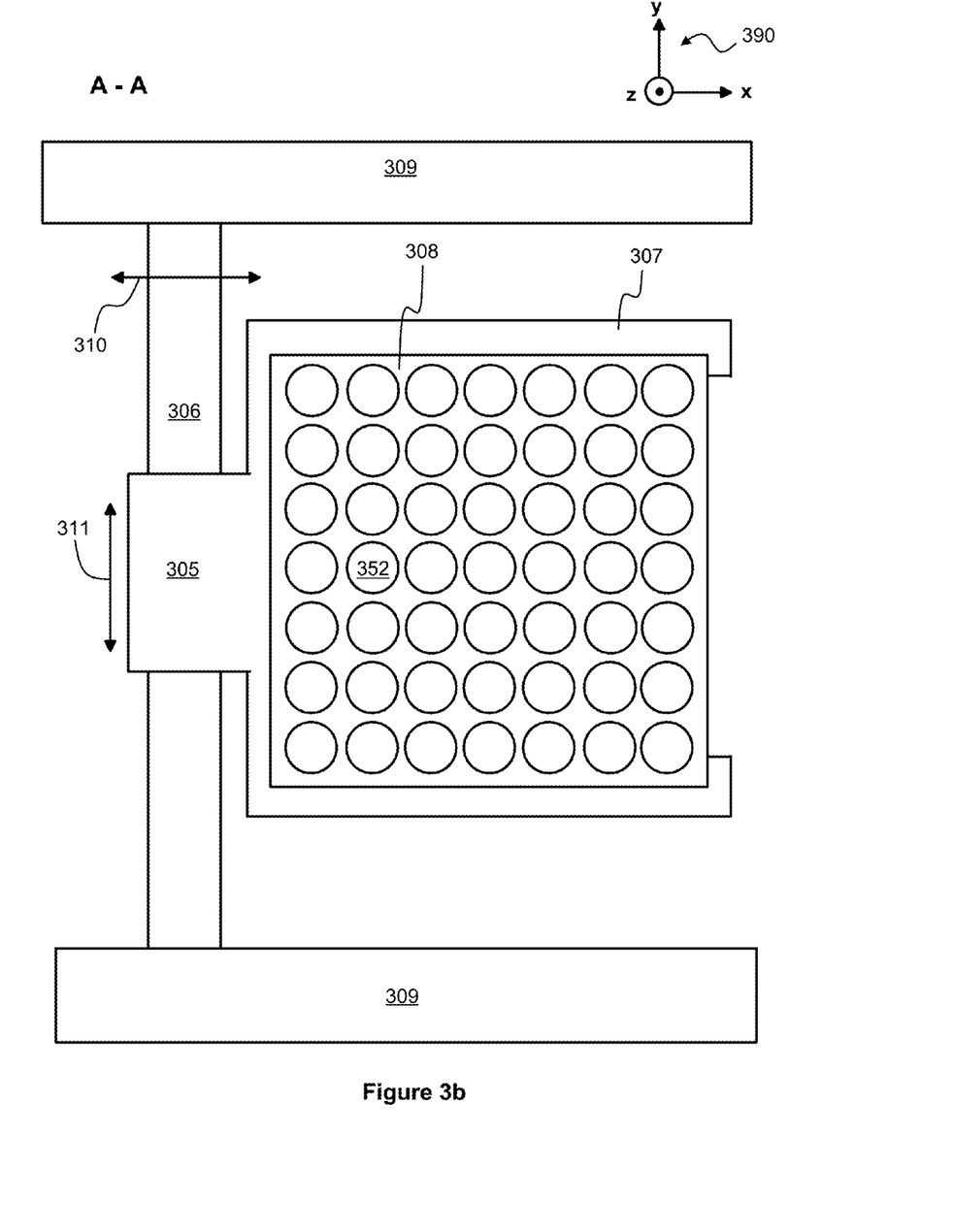

FIG. 3a shows a schematic illustration of an optical measurement instrument that comprises a device according to an exemplifying embodiment for cross-talk correction of intensities measured on two or more wavelength bands from a sample to be analyzed. FIG. 3b shows schematic illustration of a view seen downwards from the line A-A of FIG. 3a. The measurement instrument comprises mechanical support elements arranged to support a sample plate 308 that can be e.g. a microtitration plate. The sample plate comprises sample wells which contain samples 351, 352, 353, 354, 355, 356, and 357 to be analyzed. The samples have been arranged to comprise analyte-specific probe-populations, e.g. FRET-probes, in order to detect presence of two or more analytes from each sample. The mechanical support elements comprise a support rail 306 and guide elements 309 shown in FIG. 3b. The support rail 306 is supported relative to a body of the measurement instrument with the aid of the guide elements 309 in such a way that the support rail 306 is movable in the directions of a two-headed arrow 310 shown in FIG. 3b. The mechanical support elements comprise a sledge 307 capable of receiving the sample plate 308. The sledge is connected to the support rail 306 in such a way that the sledge is capable of sliding along the support rail in the longitudinal direction of the support rail, i.e. the sledge is movable with respect to the support rail 306 in the directions of a two-headed arrow 311 shown in FIG. 3b. Hence, the sample plate 308 is movable in the xy-plane defined by a co-ordinate system 390. Due to the fact that the sample wells are movable in the xy-plane, the contents of different sample wells can be measured in a temporally successive manner so that each sample well is in turn the sample well whose content is being measured.

The measurement instrument comprises measurement equipment for measuring intensities on two or more detection wavelength bands from a sample to be analyzed. Each detection wavelength band relates to one of analyte-specific probe-populations contained by the sample, and each probe-population is, after excitation, capable of emitting at least a first signal component and a second signal component whose spectra have maxima at different wavelengths and at least the first signal component is dependent on presence of analyte detectable with that probe-population. The measurement equipment comprises an excitation light source 303, FIG. 3a, and a light guide 304 for directing excitation radiation to the sample 352 being measured. The measurement equipment comprises a detector 302 for measuring, on appropriate wavelength bands, the emission radiation emitted by the sample 352 and for producing a signal indicative of intensities of the emission radiation measured on the wavelength bands. The detector 309 can be based on, for example, a photodiode or a photomultiplier tube. The measurement instrument comprises a controller 301 for controlling the operation of the excitation light source 303 and the detector 302. The excitation light source 303, the detector 302, and/or the light guide 304 can be either integral or replaceable components of the measurement instrument. The controller 301 can be can be implemented with one or more programmable processor circuits, one or more dedicated hardware circuits such as an application specific integrated circuit "ASIC", one or more field programmable logic circuits such as a field programmable gate array "FPGA", or a combination of these. Furthermore, the optical measurement instrument may comprise an optical filtering device with the aid of which an appropriate wavelength band can be selected for each measurement.

The measurement instrument comprises a device for cross-talk correction of the intensities measured on the two or more detection wavelength bands from the sample 352. The device comprises:

means for computing estimates of cross-talk intensities occurring on the detection wavelength bands and at least partially caused by the second signal components emitted by the probe-populations on the basis of: a) first cross-talk parameters and b) at least one value indicative of at least one intensity each occurring on one of auxiliary wavelength bands outside the detection wavelength bands and at least partially caused by the second signal components, and means for computing cross-talk corrected intensities of the detection wavelength bands on the basis of: a) the intensities measured on the detection wavelength bands, b) the computed estimates of the cross-talk intensities, and c) second cross-talk parameters, where:

each of the first cross-talk parameters indicates a relation between a) intensity occurring on one of the detection wavelength bands and at least partially caused by the second signal components, and b) intensity occurring on the auxiliary wavelength band and at least partially caused by the second signal components, and each of the second cross-talk parameters indicates a relation between a) intensity occurring on the detection wavelength band related to one of the probe-populations and at least partially caused by the first signal component emitted by another of the probe-populations, and b) intensity occurring on the detection wavelength band related to the other of the probe-populations and at least partially caused by the first signal component emitted by the other of the probe-populations.

In the measurement instrument illustrated in FIGS. 3a and 3b, the controller 301 comprises a computing system that is configured to constitute the device for cross-talk correction. In a measurement instrument according to another exemplifying embodiment, the device for cross-talk correction is implemented with a separate computing system.

In a device according to an exemplifying embodiment, the computing system is configured to compute the estimates of the cross-talk intensities occurring on the detection wavelength bands and at least partially caused by the second signal components according to the following equation:

$$C_{Bi} = R_{Bi} \times I_{BM},$$

where $C_{Bi}$ is the estimate of the cross-talk intensity occurring on the $i^{th}$ one of the detection wavelength bands and at least partially caused by the second signal components, $R_{Bi}$ is the first cross-talk parameter related to the $i^{th}$ one of the detection wavelength bands, and $I_{BM}$ is the value indicative of the intensity occurring on the auxiliary wavelength band and at least partially caused by the second signal components.

In a device according to an exemplifying embodiment, the computing system is configured to solve the cross-talk corrected intensities of the detection wavelength bands from the following set of equations:

$$\begin{cases} I_{C1} = I_{M1} - \sum_{j=2}^{n} R_{1j}(I_{Cj} - C_{Bj}) \\ \quad \ldots \\ I_{Ci} = I_{Mi} - \sum_{j=1, j \neq i}^{n} R_{ij}(I_{Cj} - C_{Bj}) \\ \quad \ldots \\ I_{Cn} = I_{Mn} - \sum_{j=1}^{n-1} R_{nj}(I_{Cj} - C_{Bj}) \end{cases}$$

where:
$I_{Ci}$ and $I_{Cj}$ are the cross-talk corrected intensities of the $i^{th}$ and $j^{th}$ ones of the detection wavelength bands, respectively,
$I_{Mi}$ is the intensity measured on the $i^{th}$ one of the detection wavelength bands,
$C_{Bj}$ is the estimate of the cross-talk intensity occurring on the $j^{th}$ one of the detection wavelength bands and at least partially caused by the second signal components, and
$R_{ij}$ is the second cross-talk parameter that indicates a ratio between a) intensity occurring on the $i^{th}$ one of the detection wavelength bands and at least partially caused by the first signal component emitted by the probe-population related to the $j^{th}$ one of the detection wavelength bands and b) intensity occurring on the $j^{th}$ one of the detection wavelength bands and at least partially caused by the first signal component emitted by the probe-population related to the $j^{th}$ one of the detection wavelength bands.

In a device according to an exemplifying embodiment, the computing system is configured determine the first cross-talk parameters on the basis of first test intensities measured from one or more first model samples each of which contains one or more of the probe-populations and is free from analytes detectable with the probe-populations.

In a device according to an exemplifying embodiment, the computing system is configured to compute the first cross-talk parameters according to the equation:

$$R_{Bi} = \frac{I_{Model0, i}}{I_{Model0, B}}$$

where:
$R_{Bi}$ is the first cross-talk parameter related to the $i^{th}$ one of the detection wavelength bands,
$I_{Model0, i}$ is the first test intensity occurring on $i^{th}$ one of the detection wavelength bands and at least partially caused by the second signal components and measured from such a first model sample that contains the probe-populations, and
$I_{model0, B}$ is the first test intensity occurring on the auxiliary wavelength band and at least partially caused by the second signal components and measured from the first model sample.

In a device according to an exemplifying embodiment, the computing system is configured determine the second cross-talk parameters on the basis of second test intensities measured from second model samples, where each of the second model samples contains one or more of the probe-populations and analyte detectable with one of the probe-populations and is free from analytes detectable with the other probe-populations.

In a device according to an exemplifying embodiment, the computing system is configured to compute the second cross-talk parameters according to the equation:

$$R_{ij} = \frac{I_{Model, i, j} - C_i}{I_{Model, j, j} - C_j}$$

where:
$R_{ij}$ is the second cross-talk parameter related to the $i^{th}$ and $j^{th}$ ones of the detection wavelength bands,
$I_{Model, i, j}$ is the second test intensity occurring on the $i^{th}$ one of the detection wavelength bands and at least partially caused by the first signal component emitted by the probe-population related to the $j^{th}$ one of the detection wavelength bands and measured from the second model sample that contains analyte detectable with the probe-population related to the $j^{th}$ one of the detection wavelength bands and is free from analytes detectable with the other probe-populations,
$I_{Model, j, j}$ is the second test intensity occurring on the $j^{th}$ one of the detection wavelength bands and at least partially caused by the first signal component emitted by the probe-population related to the $j^{th}$ one of the detection wavelength bands and measured from the second model sample, and
$C_i$ and $C_j$ are real valued adjustment terms.

In a device according to an exemplifying embodiment, the computing system is configured to set the adjustment terms so that the above-mentioned $C_i = R_{Bi} \times$ intensity at least partially caused by the second signal components and measured on the auxiliary wavelength band from the above-mentioned second model sample, and the above-mentioned $C_j = R_{Bj} \times$ intensity at least partially caused by the second signal components and measured on the auxiliary wavelength band from the second model sample, where $R_{Bi}$ and $R_{Bj}$ are the first cross-talk parameters related to the $i^{th}$ and $j^{th}$ ones of the detection wavelength bands, respectively.

In a device according to an exemplifying embodiment, the computing system is configured to set the adjustment terms so that $C_i$ is test intensity occurring on $i^{th}$ one of the detection wavelength bands and at least partially caused by the second signal components, and $C_j$ is test intensity occurring on $j^{th}$ one of the detection wavelength bands and at least partially caused by the second signal components, where the test intensities $C_i$ and $C_j$ are measured from a model sample that contains the probe-populations and is free from analytes detectable with the probe-populations.

In a device according to an exemplifying embodiment, the computing system is configured to set the adjustment terms so that $C_i = C_j = 0$.

In a measurement instrument according to an exemplifying embodiment, the measurement equipment is configured to measure the intensity occurring on the auxiliary wavelength band and at least partially caused by the second signal components from the sample 352, and the device for cross-talk correction is configured to use the measured intensity when computing the estimates of the cross-talk intensities occurring on the detection wavelength bands and at least partially caused by the second signal components.

In a measurement instrument according to an exemplifying embodiment, the device for cross-talk correction is configured to select the first and second cross-talk parameters from among pre-determined values on the basis of at least one of the following: ways of conduct of intensity measurements, information identifying the measurement instrument from among similar measurement instruments. The information identifying a measurement instrument can be, for example, a serial number of the measurement instrument.

The specific examples provided in the description given above should not be construed as limiting. Therefore, the protection scope is not limited merely to the embodiments described above.

The invention claimed is:

1. A method for cross-talk correction of intensities measured on two or more detection wavelength bands from a sample, each detection wavelength band relating to one of analyte-specific probe-populations contained by the sample and each probe-population being capable of emitting a first signal component and a second signal component whose spectra are mutually different and at least the first signal component being dependent on presence of analyte detectable with that probe-population, the method comprising:

computing estimates of cross-talk intensities occurring on the detection wavelength bands and at least partially caused by the second signal components emitted by the probe-populations on the basis of: a) first cross-talk parameters and b) at least one value indicative of at least one intensity occurring on at least one auxiliary wavelength band outside the detection wavelength bands and at least partially caused by the second signal components, and computing cross-talk corrected intensities of the detection wavelength bands on the basis of: a) the intensities measured on the detection wavelength bands, b) the computed estimates of the cross-talk intensities, and c) second cross-talk parameters, wherein:

each of the first cross-talk parameters indicates a relation between a) intensity occurring on one of the detection wavelength bands and at least partially caused by the second signal components, and b) intensity occurring on the auxiliary wavelength band and at least partially caused by the second signal components, and the first cross-talk parameters being obtained on the basis of first test intensities measurable from one or more first model samples each of which contains one or more of the analyte-specific probe-populations and is free from analytes detectable with the probe-populations, and each of the second cross-talk parameters indicates a relation between a) intensity occurring on the detection wavelength band related to one of the probe-populations and at least partially caused by the first signal component emitted by another of the probe-populations, and b) intensity occurring on the detection wavelength band related to the other of the probe-populations and at least partially caused by the first signal component emitted by the other of the probe-populations.

2. A method according to claim 1, wherein the estimates of the cross-talk intensities occurring on the detection wavelength bands and at least partially caused by the second signal components are computed according to the following equation:

$$C_{Bi} = R_{Bi} \times I_{BM},$$

where $C_{Bi}$ is the estimate of the cross-talk intensity occurring on the $i^{th}$ one of the detection wavelength bands and at least partially caused by the second signal components, $R_{Bi}$ is the first cross-talk parameter related to the $i^{th}$ one of the detection wavelength bands, and $I_{BM}$ is the value indicative of the intensity occurring on the auxiliary wavelength band and at least partially caused by the second signal components.

3. A method according to claim 1, wherein the cross-talk corrected intensities of the detection wavelength bands are solved from the following set of equations:

$$\begin{cases} I_{C1} = I_{M1} - \sum_{j=2}^{n} R_{1j}(I_{Cj} - C_{Bj}) \\ \quad \ldots \\ I_{Ci} = I_{Mi} - \sum_{j=1, j \neq i}^{n} R_{ij}(I_{Cj} - C_{Bj}) \\ \quad \ldots \\ I_{Cn} = I_{Mn} - \sum_{j=1}^{n-1} R_{nj}(I_{Cj} - C_{Bj}) \end{cases}$$

where:

$I_{Ci}$ and $I_{Cj}$ are the cross-talk corrected intensities of the $i^{th}$ and $j^{th}$ ones of the detection wavelength bands, respectively, $I_{Mi}$ is the intensity measured on the $i^{th}$ one of the detection wavelength bands, $C_{Bj}$ is the estimate of the cross-talk intensity occurring on the $j^{th}$ one of the detection wavelength bands and at least partially caused by the second signal components, and $R_{ij}$ is the second cross-talk parameter that indicates a ratio between a) intensity occurring on the $i^{th}$ one of the detection wavelength bands and at least partially caused by the first signal component emitted by the probe-population related to the $j^{th}$ one of the detection wavelength bands and b) intensity occurring on the $j^{th}$ one of the detection wavelength bands and at least partially caused by the first signal component emitted by the probe-population related to the $j^{th}$ one of the detection wavelength bands.

4. A method according to claim 1, wherein the method comprises determining the first cross-talk parameters on the basis of the first test intensities measured from the one or more first model samples each of which contains the one or more of the probe-populations and is free from the analytes detectable with the probe-populations.

5. A method according to claim 4, wherein the first cross-talk parameters are computed according to the equation:

$$R_{Bi} = \frac{I_{Model0,i}}{I_{Model0,B}}$$

where:

$R_{Bi}$ is the first cross-talk parameter related to the $i^{th}$ one of the detection wavelength bands, $I_{Model0,1}$ is the first test intensity occurring on $i^{th}$ one of the detection wavelength bands and at least partially caused by the second signal components and measured from the such first model sample that contains the probe-populations, and $I_{Model0,B}$ is the first test intensity occurring on the auxiliary wavelength band and at least partially caused by the second signal components and measured from the first model sample.

6. A method according to claim 1, wherein the method comprises determining the second cross-talk parameters on the basis of second test intensities measured from second model samples, each of the second model samples containing one or more of the probe-populations and analyte detectable with one of the probe-populations and being free from analytes detectable with the other probe-populations.

7. A method according to claim 6, wherein the second cross-talk parameters are computed according to the equation:

$$R_{ij} = \frac{I_{Model,i,j} - C_i}{I_{Model,j,j} - C_j}$$

where:
$R_{ij}$ is the second cross-talk parameter related to the $i^{th}$ and $j^{th}$ ones of the detection wavelength bands, $I_{Model, i,j}$ is the second test intensity occurring on the $i^{th}$ one of the detection wavelength bands and at least partially caused by the first signal component emitted by the probe-population related to the $j^{th}$ one of the detection wavelength bands and measured from the second model sample that contains analyte detectable with the probe-population related to the $j^{th}$ one of the detection wavelength bands and is free from analytes detectable with the other probe-populations, $I_{Model, j,j}$ is the second test intensity occurring on the $j^{th}$ one of the detection wavelength bands and at least partially caused by the first signal component emitted by the probe-population related to the $j^{th}$ one of the detection wavelength bands and measured from the second model sample, and $C_i$ and $C_j$ are real valued adjustment terms.

8. A method according to claim 7, wherein $C_i=C_j=0$.

9. A method according to claim 7, wherein $C_i$ is test intensity occurring on $i^{th}$ one of the detection wavelength bands and at least partially caused by the second signal components, and $C_j$ is test intensity occurring on $j^{th}$ one of the detection wavelength bands and at least partially caused by the second signal components, the test intensities $C_i$ and $C_j$ being measured from a model sample that contains one or more of the probe-populations and is free from analytes detectable with the probe-populations.

10. A method according to claim 7, wherein $C_i=R_{Bi}\times$ intensity that is at least partially caused by the second signal components and measured on the auxiliary wavelength band from the second model sample, and $C_j=R_{Bj}\times$ intensity at least partially caused by the second signal components and measured on the auxiliary wavelength band from the second model sample, where $R_{Bi}$ and $R_{Bj}$ are the first cross-talk parameters related to the $i^{th}$ and $j^{th}$ ones of the detection wavelength bands, respectively.

11. A method according to claim 1, wherein the value indicative of the intensity occurring on the auxiliary wavelength band and at least partially caused by the second signal components is a value measured from the sample on the auxiliary wavelength band.

12. A method according to claim 1, wherein the first and second cross-talk parameters are selected from among predetermined values on the basis of at least one of the following: ways of conduct of intensity measurements, information identifying a measurement instrument used for the intensity measurements.

13. A method according to claim 1, wherein the probe-populations are populations of probes based on fluorescence resonance energy transfer where each probe comprises at least one donor, at least one acceptor, and at least one reactive region capable of interacting with analyte to be detected with that probe.

14. A method according to claim 13, wherein the donor is a luminescent label having luminescent lifetime longer than 1 μs.

15. A method according to claim 13, wherein the donor is a lanthanide chelate donor and the acceptor is an organic fluorophore acceptor.

16. A method according to claim 15, wherein the lanthanide is europium, terbium, dysprosium, or samarium.

17. A device for cross-talk correction of intensities measured on two or more detection wavelength bands from a sample, each detection wavelength band relating to one of analyte-specific probe-populations contained by the sample and each probe-population being capable of emitting a first signal component and a second signal component whose spectra are mutually different and at least the first signal component being dependent on presence of analyte detectable with that probe-population, the device comprising a computing system configured to:

compute estimates of cross-talk intensities occurring on the detection wavelength bands and at least partially caused by the second signal components emitted by the probe-populations on the basis of: a) first cross-talk parameters and b) at least one value indicative of at least one intensity occurring on at least one auxiliary wavelength band outside the detection wavelength bands and at least partially caused by the second signal components, and compute cross-talk corrected intensities of the detection wavelength bands on the basis of: a) the intensities measured on the detection wavelength bands, b) the computed estimates of the cross-talk intensities, and c) second cross-talk parameters, wherein:

each of the first cross-talk parameters indicates a relation between a) intensity occurring on one of the detection wavelength bands and at least partially caused by the second signal components, and b) intensity occurring on the auxiliary wavelength band and at least partially caused by the second signal components, and the first cross-talk parameters being obtained on the basis of first test intensities measurable from one or more first model samples each of which contains one or more of the analyte-specific probe-populations and is free from analytes detectable with the probe-populations, and each of the second cross-talk parameters indicates a relation between a) intensity occurring on the detection wavelength band related to one of the probe-populations and at least partially caused by the first signal component emitted by another of the probe-populations, and b) intensity occurring on the detection wavelength band related to the other of the probe-populations and at least partially caused by the first signal component emitted by the other of the probe-populations.

18. A device according to claim 17, wherein the computing system is configured to compute the estimates of the cross-talk intensities occurring on the detection wavelength bands and at least partially caused by the second signal components according to the following equation:

$$C_{Bi} = R_{Bi} \times I_{BM},$$

where $C_{Bi}$ is the estimate of the cross-talk intensity occurring on the $i^{th}$ one of the detection wavelength bands and at least partially caused by the second signal components, $R_{Bi}$ is the first cross-talk parameter related to the $i^{th}$ one of the detection wavelength bands, and $I_{BM}$ is the value indicative of the intensity occurring on the auxiliary wavelength band and at least partially caused by the second signal components.

19. A device according to claim 17, wherein the computing system is configured to solve the cross-talk corrected intensities of the detection wavelength bands from the following set of equations:

$$\begin{cases} I_{C1} = I_{M1} - \sum_{j=2}^{n} R_{1j}(I_{Cj} - C_{Bj}) \\ \ldots \\ I_{Ci} = I_{Mi} - \sum_{j=1, j \neq i}^{n} R_{ij}(I_{Cj} - C_{Bj}) \\ \ldots \\ I_{Cn} = I_{Mn} - \sum_{j=1}^{n-1} R_{nj}(I_{Cj} - C_{Bj}) \end{cases}$$

where:
$I_{Ci}$ and $I_{Cj}$ are the cross-talk corrected intensities of the $i^{th}$ and $j^{th}$ ones of the detection wavelength bands, respectively,
$I_{Mi}$ is the intensity measured on the $i^{th}$ one of the detection wavelength bands,
$C_{Bj}$ is the estimate of the cross-talk intensity occurring on the $j^{th}$ one of the detection wavelength bands and at least partially caused by the second signal components, and
$R_{ij}$ is the second cross-talk parameter that indicates a ratio between a) intensity occurring on the $i^{th}$ one of the detection wavelength bands and at least partially caused by the first signal component emitted by the probe-population related to the $j^{th}$ one of the detection wavelength bands and b) intensity occurring on the $j^{th}$ one of the detection wavelength bands and at least partially caused by the first signal component emitted by the probe-population related to the $j^{th}$ one of the detection wavelength bands.

20. A device according to claim 17, wherein the computing system is configured determine the first cross-talk parameters on the basis of the first test intensities measured from the one or more first model samples each of which contains the one or more of the probe-populations and is free from the analytes detectable with the probe-populations.

21. A device according to claim 20, wherein the computing system is configured to compute the first cross-talk parameters according to the equation:

$$R_{Bi} = \frac{I_{Model0,i}}{I_{Model0,B}}$$

where:
$R_{Bi}$ is the first cross-talk parameter related to the $i^{th}$ one of the detection wavelength bands,
$I_{Model0,i}$ is the first test intensity occurring on $i^{th}$ one of the detection wavelength bands and at least partially caused by the second signal components and measured from the such first model sample that contains the probe-populations, and
$I_{Model0,B}$ is the first test intensity occurring on the auxiliary wavelength band and at least partially caused by the second signal components and measured from the first model sample.

22. A device according to claim 17, wherein the computing system is configured determine the second cross-talk parameters on the basis of second test intensities measured from second model samples, each of the second model samples containing one or more of the probe-populations and analyte detectable with one of the probe-populations and being free from analytes detectable with the other probe-populations.

23. A device according to claim 22, wherein the computing system is configured to compute the second cross-talk parameters according to the equation:

$$R_{ij} = \frac{I_{Model,i,j} - C_i}{I_{Model,j,j} - C_j}$$

where:
$R_{ij}$ is the second cross-talk parameter related to the $i^{th}$ and $j^{th}$ ones of the detection wavelength bands,
$I_{Model, i,j}$ is the second test intensity occurring on the $i^{th}$ one of the detection wavelength bands and at least partially caused by the first signal component emitted by the probe-population related to the $j^{th}$ one of the detection wavelength bands and measured from the second model sample that contains analyte detectable with the probe-population related to the $j^{th}$ one of the detection wavelength bands and is free from analytes detectable with the other probe-populations,
$I_{Model, j,j}$ is the second test intensity occurring on the $j^{th}$ one of the detection wavelength bands and at least partially caused by the first signal component emitted by the probe-population related to the $j^{th}$ one of the detection wavelength bands and measured from the second model sample, and
$C_i$ and $C_j$ are real valued adjustment terms.

24. A device according to claim 23, wherein the computing system is configured to set the adjustment terms so that $C_i = C_j = 0$.

25. A device according to claim 23, wherein the computing system is configured to set the adjustment terms so that $C_i$ is test intensity occurring on $i^{th}$ one of the detection wavelength bands and at least partially caused by the second signal components, and C is test intensity occurring on $j^{th}$ one of the detection wavelength bands and at least partially caused by the second signal components, the test intensities $C_i$ and $C_j$ being measured from a model sample that contains one or more of the probe-populations and is free from analytes detectable with the probe-populations.

26. A device according to claim 23, wherein the computing system is configured to set the adjustment terms so that $C_i = R_{Bi} \times$intensity at least partially caused by the second signal components and measured on the auxiliary wavelength band from the second model sample, and $C_j = R_{Bj} \times$ intensity at least partially caused by the second signal components and measured on the auxiliary wavelength band from the second model sample, where $R_{Bi}$ and $R_{Bj}$ are the first cross-talk parameters related to the $i^{th}$ and $j^{th}$ ones of the detection wavelength bands, respectively.

27. A device according to claim 17, wherein the computing system comprises:
    a processor for executing instructions, and
    a memory for storing a computer program defining a set of instructions for controlling the processor to compute the estimates of the cross-talk intensities occurring on the detection wavelength bands and to compute the cross-talk corrected intensities of the detection wavelength bands.

28. A measurement instrument comprising:
    measurement equipment (302, 303, 304) for measuring intensities on two or more detection wavelength bands from a sample, each detection wavelength band relating to one of analyte-specific probe-populations contained by the sample and each probe-population being capable of emitting a first signal component and a second signal component whose spectra are mutually different and at least the first signal component being dependent on presence of analyte detectable with that probe-population, and
    a device according for cross-talk correction of the intensities measured on the two or more detection wavelength bands from the sample,
    the device comprising a computing system configured to:
        compute estimates of cross-talk intensities occurring on the detection wavelength bands and at least partially caused by the second signal components emitted by the probe-populations on the basis of: a) first cross-talk parameters and b) at least one value indicative of at least one intensity occurring on at least one auxiliary wavelength band outside the detection wavelength bands and at least partially caused by the second signal components, and
        compute cross-talk corrected intensities of the detection wavelength bands on the basis of: a) the intensities measured on the detection wavelength bands, b) the computed estimates of the cross-talk intensities, and c) second cross-talk parameters,
    wherein:
        each of the first cross-talk parameters indicates a relation between a) intensity occurring on one of the detection wavelength bands and at least partially caused by the second signal components, and b) intensity occurring on the auxiliary wavelength band and at least partially caused by the second signal components, and the first cross-talk parameters being obtained on the basis of first test intensities measurable from one or more first model samples each of which contains one or more of the analyte-specific probe-populations and is free from analytes detectable with the probe-populations, and
        each of the second cross-talk parameters indicates a relation between a) intensity occurring on the detection wavelength band related to one of the probe-populations and at least partially caused by the first signal component emitted by another of the probe-populations, and b) intensity occurring on the detection wavelength band related to the other of the probe-populations and at least partially caused by the first signal component emitted by the other of the probe-populations.

29. A measurement instrument according to claim 28, wherein the measurement equipment is configured to measure the intensity occurring on the auxiliary wavelength band and at least partially caused by the second signal components from the sample, and the device for cross-talk correction is configured to use the measured intensity when computing the estimates of the cross-talk intensities occurring on the detection wavelength bands and at least partially caused by the second signal components.

30. A measurement instrument according to claim 28, wherein the device for cross-talk correction is configured to select the first and second cross-talk parameters from among pre-determined values on the basis of at least one of the following: ways of conduct of intensity measurements, information identifying the measurement instrument from among similar measurement instruments.

31. A non-transitory computer readable medium encoded with a computer program for cross-talk correction of intensities measured on two or more detection wavelength bands from a sample, each detection wavelength band relating to one of analyte-specific probe-populations contained by the sample and each probe-population being capable of emitting a first signal component and a second signal component whose spectra are mutually different and at least the first signal component being dependent on presence of analyte detectable with that probe-population, wherein the computer program comprises computer executable instructions for controlling a programmable processor to:
    compute estimates of cross-talk intensities occurring on the detection wavelength bands and at least partially caused by the second signal components emitted by the probe-populations on the basis of: a) first cross-talk parameters and b) at least one value indicative of at least one intensity occurring on at least one auxiliary wavelength band outside the detection wavelength bands and at least partially caused by the second signal components, and
    compute cross-talk corrected intensities of the detection wavelength bands on the basis of: a) the intensities measured on the detection wavelength bands, b) the computed estimates of the cross-talk intensities, and c) second cross-talk parameters,
wherein:
    each of the first cross-talk parameters indicates a relation between a) intensity occurring on one of the detection wavelength bands and at least partially caused by the second signal components, and b) intensity occurring on the auxiliary wavelength band and at least partially caused by n-t second signal components, and the first cross-talk parameters being obtained on the basis of first test intensities measurable from one or more first model samples each of which contains one or more of the analyte-specific probe-populations and is free from analytes detectable with the probe-populations, and
    each of the second cross-talk parameters indicates a relation between a) intensity occurring on the detection wavelength band related to one of the probe-populations and at least partially caused by the first signal component emitted by another of the probe-populations, and b) intensity occurring on the detection wavelength band related to the other of the probe-populations and at least partially caused by the first signal component emitted by the other of the probe-populations.

* * * * *